United States Patent [19]

Metzner et al.

[11] Patent Number: 4,824,484

[45] Date of Patent: Apr. 25, 1989

[54] AGENT FOR PRESERVING WOOD OR WOOD-BASED MATERIALS AND METHOD FOR PREPARATION AND USE THEREOF

[75] Inventors: Wolfgang Metzner; Detlef Seepe, both of Krefeld, Fed. Rep. of Germany

[73] Assignee: Desowag Materialschutz GmbH, Duesseldorf, Fed. Rep. of Germany

[21] Appl. No.: 187,209

[22] Filed: Apr. 28, 1988

[30] Foreign Application Priority Data

Apr. 28, 1987 [DE] Fed. Rep. of Germany ....... 3714051

[51] Int. Cl.$^4$ .......................... C09D 5/14; B05D 1/00
[52] U.S. Cl. .............................. 106/18.31; 106/18.32; 106/14.12; 106/14.15; 514/114; 514/642; 514/643; 427/297; 427/440
[58] Field of Search .............. 106/18.31, 18.32, 14.12, 106/14.15; 514/114, 642, 643; 427/297, 440

[56] References Cited

U.S. PATENT DOCUMENTS

| | | | |
|---|---|---|---|
| 3,247,059 | 4/1966 | Bauer | 424/166 |
| 4,132,572 | 1/1979 | Parant et al. | 106/14.12 |
| 4,613,450 | 9/1986 | Moran et al. | 106/14.12 |
| 4,767,458 | 8/1988 | Moewius et al. | 106/18.31 |

FOREIGN PATENT DOCUMENTS 3336557 4/1985 Fed. Rep. of Germany .

*Primary Examiner*—Paul Lieberman
*Assistant Examiner*—Helene Kirschner

*Attorney, Agent, or Firm*—Foley & Lardner, Schwartz, Jeffery, Schwaab, Mack, Blumenthal & Evans

[57] ABSTRACT

The present invention relates to a wood preservative comprising either (1) at least one of (a) ammonium monofluorophosphate and/or diammonium monofluorophosphate of the general formula $(R_1R_2R_3R_4N)R_5PO_3F$ in which $R_1$, $R_2$, $R_3$ and $R_4$ are identical or different and each denotes a straight-chain, branched or cyclic, saturated or unsaturated alkyl, aralkyl, alkyaryl or aryl radical, either unsubstituted or substituted by an alkyl, alkoxy or a hydroxyl group, up to three of the four $R_1$–$R_4$ can be hydrogen or can together form an alkylene bridge, $R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively, and (b) a mixture of a salt of monofluorophosphoric acid and at least one ammonium salts of the general formula $R_1R_2R_3R_4NX$ in which X is an acid radical, or (2) a mixture of (a) and/or (b) and (c) an alkali metal monofluorophosphate or an ammonium monofluorophosphate of the general formula $M_2PO_3F$ and/or $MHPO_3F$, in which M is sodium, potassium or ammonium. The present invention also relates to a coating agent comprising an ammonium monofluorophosphate as above and components (d) that comprises at least one of a binder, a fixing agent and a plasticizer, and (e) a diluent, and to methods of producing and using such agents.

29 Claims, No Drawings

AGENT FOR PRESERVING WOOD OR WOOD-BASED MATERIALS AND METHOD FOR PREPARATION AND USE THEREOF

BACKGROUND OF THE INVENTION

The present invention relates to an agent for preserving wood and wood-based materials (hereafter also referred to as "wood preservative"), based on at least one ammonium monofluorophosphate, the agent comprising either (1) at least one of the group consisting of (a) an organic ammonium monofluorophosphate and/or an organic diammonium monofluorophosphate and (b) a mixture of a salt of monofluorophosphoric acid in a solvent with at least one ammonium salt, or (2) a mixture of at least one of (a) and (b) mentioned above and (c) an alkali metal monofluorophosphate or ammonium monofluorophosphate of the general formula $M_2PO_3F$ and/or $MHPO_3F$, wherein M is sodium, potassium and/or ammonium This invention also relates to a coating agent for wood and wood-based materials comprising an agent as described above as well as components (d) comprising at least one of a binder, a fixing agent and a plasticizer, and (e) a diluent.

This invention further relates to a method of treating wood by use of a wood preservative as described above, a method of coating wood by a coating agent as described above and a method of producing the preservative and coating agent.

An agent for preserving wood and wood-based materials based on at least one alkali metal salt containing fluorine or fluorine ions is known from German Offenlegungsschrift No. 3,336,557, the wood preservative comprising, as the alkali metal salt, a monofluorophosphate and/or a difluorphosphate of the general formula $M_2PO_3F$ and/or $MPO_3F_2$, in which M denotes sodium, potassium and/or ammonium. This wood preservative has a good wood-protecting action. However, certain reductions in action occur upon exposure, for example, upon long-term outdoor weathering.

SUMMARY OF THE INVENTION

It is, therefore, an object of the present invention to provide an improved, in particular, a chromate-free wood-preservative that has both fungicidal and insecticidal action and an improved long-term action upon exposure (fixations).

It is another object of the present invention to provide an agent for preserving wood or wood-based materials, which agent is soluble in at least some organic solvents and in water so that the range of applications can be extended.

It is a further object of the present invention to provide a method for treating wood or wood-based materials by use of the agent described above.

It is yet another object of the present invention to provide an agent for coating wood or wood-based materials.

It is a still further object of the present invention to provide a method for coating wood or wood-based materials.

In accomplishing these and other objects, there has been provided an agent for preserving wood or wood-based materials comprising ammonium monofluorophosphate selected from the group consisting of (1) at least one of components (a) and (b), and (2) a mixture of components (a) and/or (b) and component (c), wherein component comprises an or organic ammonium monofluorophosphate and/or an organic diammonium monofluorophosphate of the formula $$(R_1R_2R_3R_4N)R_5PO_3F \qquad \text{(Formula I)}$$

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$–$R_4$ can be hydrogen or can together form an alkylene bridge;

$R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively;

(b) comprises a mixture of a salt of monofluorophosphoric acid in a solvent with at least one ammonium salt of the formula $$R_1R_2R_3R_4NX \qquad \text{(Formula II)}$$

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $$M_2PO_3F \text{ and/or}$$

$$MHPO_3F$$

wherein M is at least one of sodium, potassium and ammonium.

In accordance with another aspect of the present invention, there has been provided a method of preserving wood or wood-based materials comprising the step of treating said materials with an agent that comprises an ammonium monofluorophosphate composition selected from the group consisting of (1) at least one of components (a) and (b), and (2) a mixture of components (a) and/or (b) and component (c), wherein component (a) comprises an organic ammonium monofluorophosphate and/or an organic diammonium monofluorophosphate of the formula $$(R_1R_2R_3R_4N)R_5PO_3F \qquad \text{(Formula I)}$$

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$–$R_4$ can be hydrogen or can together form an alkylene bridge;

$R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively;

(b) comprises a mixture of a salt of monofluorophosphoric acid in a solvent with at least one ammonium salt of the formula $$R_1R_2R_3R_4NX \quad \text{(Formula II)}$$

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $$M_2PO_3F \text{ and/or}$$

$$MHPO_3F$$

wherein M is at least one of sodium, potassium and ammonium.

In accordance with yet another aspect of the present invention, there has been provided a coating agent for wood or wood-based materials comprising ammonium monofluorophosphate selected from the group consisting of (1) at least one of components (a) and (b), and (2) a mixture of components (a) and/or (b) and component (c),
component (d) and
component (e),
wherein component (a) comprises an organic ammonium monofluorophosphate and/or an organic diammonium monofluorophosphate of the formula $$(R_1R_2R_3R_4N)R_5PO_3F \quad \text{(Formula I)}$$

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$-$R_4$ can be hydrogen or can together form an alkylene bridge;

$R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively;

(b) comprises a mixture of a salt of monofluorophosphoric acid in a solvent with at least one ammonium salt of the formula $$R_1R_2R_3R_4NX \text{ (Formula II )}$$

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $$M_2PO_3F \text{ and/or}$$

$$MHPO_3F$$

wherein M is at least one of sodium, potassium and ammonium;

(d) comprises at least one of a binder, a fixing agent and a plasticizer; and (e) comprises a diluent.

In accordance with still another aspect of the present invention, there has been provided a method of using a coating agent comprising the step of applying said coating agent to the surface of a wood or wood-based material, wherein said coating agent comprises ammonium monofluorophosphate selected from the group consisting of (1) at least one of components (a) and (b), and (2) a mixture of components (a) and/or (b) and component (c),
component (d), and
component (e),
wherein component (a) comprises an organic ammonium monofluorophosphate and/or an organic diammonium monofluorophosphate of the formula $$(R_1R_2R_3R_4N)R_5PO_3F \quad \text{(Formula I)}$$

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$-$R_4$ can be hydrogen or can together form an alkylene bridge;

$R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively;

(b) comprises a mixture of a salt of monofluorophosphoric acid in a solvent with at least one ammonium salt of the formula $$R_1R_2R_3R_4NX \quad \text{(Formula 11)}$$

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $$M_2PO_3F \text{ and/or}$$

$$MHPO_3F$$

wherein M is at least one of sodium, potassium and ammonium;

(d) comprises at least one of a binder, a fixing agent and a plasticizer; and (e) comprises a diluent.

In accordance with a further aspect of the present invention, there has been provided a method of producing an agent for preserving wood or wood-based material comprising the steps of reacting a predetermined amount of an ammonium salt with a predetermined amount of a monofluorophosphate in a solvent or diluent at a temperature between about 5° C. and about 80° C., and mixing the products of the above reaction with other components of said agent at a temperature of between about 5° C. and about 80° C., wherein said ammonium salt is represented by the formula $$R_1R_2R_3R_4NX,$$

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$–$R_4$ can be hydrogen or can together form an alkylene bridge; and X denotes an acid radical; and
said monofluorophosphate is represented by the formula $M_2PO_3F$ and/or $MHPO_3F$ wherein M is at least one of an alkali metal and ammonium.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has been discovered that the abovementioned objects can be achieved by an agent for preserving wood and wood-based materials, based upon at least one ammonium monofluorophosphate, which agent comprises, as ammonium monofluorophosphate, (a) an organic ammonium monofluorophosphate and/or an organic diammonium monofluorophosphate of the general formula $(R_1R_2R_3R_4N)R_5PO_3F$ in which $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and a maximum of three of the substituents can be hydrogen or can together form an alkylene bridge; $R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively, and/or (b) a mixture of a salt of monofluorophosphoric acid in a solvent with at least one ammonium salt of the general formula $R_1R_2R_3R_4NX$ in which $R_1$, $R_2$, $R_3$ and $R_4$, respectively, have the above-mentioned meanings and X denotes an acid radical, and/or (c) a mixture of (a) and/or (b) and an alkali metal monofluorophosphate or an ammonium monofluorophosphate of the formula $M_2PO_3F$ and/or $MHPO_3F$, wherein M is sodium, potassium and/or ammonium.

According to a preferred embodiment, the wood preservative additionally comprises at least one biocidal and/or fire-inhibiting chemical compound or a mixture of compounds that comprises, as at least one component, a biocidal and/or fire-inhibiting chemical compound and/or at least one wetting agent, emulsifier, dye and/or pigment.

According to another preferred embodiment, the wood preservative comprises about 99.95% to about 94% by weight, preferably about 99.8% to about 96% by weight, of at least one ammonium monofluorophosphate (a) of the general formula $(R_1R_2R_3R_4N)R_5PO_3F$ in which $R_1$, $R_2$, $R_3$ and $R_4$ are identical or different and each denotes a straight-chain, branched or cyclic, saturated or unsaturated alkyl, aralkyl, alkylaryl or aryl radical, where these may optionally be substituted by an alkyl, alkoxy or a hydroxyl group, and a maximum of three of the substituents may alternatively be hydrogen or together form an alkylene bridge; $R_5$ is a hydrogen atom or a $R_6R_7R_8R_9N$ group in which $R_6$, $R_7$, $R_8$ and $R_9$, respectively, may have the same meanings as $R_1$, $R_2$, $R_3$ and $R_4$, respectively, and/or (b) in a mixture of a salt of monofluorophosphoric acid in a solvent and at least one ammonium salt of the general formula $R_1R_2R_3R_4NX$ in which $R_1$, $R_2$, $R_3$ and $R_4$, respectively, have the above-mentioned meanings and X denotes an acid radical, and/or (c) in a mixture of (a) and/or (b) and an alkali metal monofluorophosphate or an ammonium monofluorophosphate of the formula $M_2PO_3F$ and/or $MHPO_3F$, wherein M is sodium, potassium and/or ammonium, and about 0.5% to about 6% by weight, preferably about 0.2% to about 4% by weight, of at least one wetting agent, emulsifier, dye and/or pigment.

According to another preferred embodiment, the wood preservative comprises a mixture of about 0.1% to about 80% by weight, preferably about 10% to about 75% by weight, of at least one ammonium monofluorophosphate (a) of the general formula $(R_1R_2R_3R_4N)R_5PO_3F$ in which $R_1$, $R_2$, $R_3$ and $R_4$ are identical or different and each denotes a straight-chain, branched or cyclic, saturated or unsaturated alkyl, aralkyl, alkylaryl or aryl radical, where these may optionally be substituted by an alkyl, alkoxy or a hydroxyl group, and a maximum of three of the substituents may alternatively be hydrogen or together form an alkylene bridge; $R_5$ is a hydrogen atom or a $R_6R_7R_8R_9N$ group in which $R_6$, $R_7$, $R_8$ and $R_9$, respectively, may have the same meanings as $R_1$, $R_2$, $R_3$ and $R_4$, respectively, and/or (b) in a mixture of a salt of monofluorophosphoric acid in a solvent and at least one ammonium salt of the general formula $R_1R_2R_3R_4NX$ in which $R_1$, $R_2$, $R_3$ and $R_4$, respectively, have the above-mentioned meanings and X denotes an acid radical, and/or (c) in a mixture of (a) and/or (b) and an alkali metal monofluorophosphate or an ammonium monofluorophosphate of the formula $M_2PO_3F$ and/or $MHPO_3F$, wherein M is sodium, potassium and/or ammonium, and about 99.85% to about 15% by weight, preferably about 89.9% to about 22% by weight, of at least one biocidal and/or fire-inhibiting chemical compound or a mixture of compounds which comprises, as at least one component, a biocidal and/or fire-inhibiting chemical compound, and comprises about 0.05% to about 5% by weight, preferably about 0.2% to about 3% by weight, of at least one wetting agent, emulsifier, dye and/or pigment.

The wood preservative can additionally comprise, as a biocidal and/or fire-inhibiting compound, at least one biocidal inorganic or organic compound and/or a fire-inhibiting inorganic compound or an inorganic and/or organic mixture of compounds that comprises, as at least one component, a biocidal and/or fire-inhibiting inorganic compound.

The wood preservative comprises, as biocidal and/or fire-inhibiting inorganic compound, at least one water-soluble alkali metal salt and/or an ammonium salt, preferably an alkali metal salt and/or an ammonium salt of phosphoric acid, polyphosphoric acid, hydrofluoric acid, boric acid, fluoroboric acid and/or an ammonium, magnesium, copper and/or zinc salt, preferably a chloride, sulfate, fluoride or silicofluoride, or one of its salts or compounds with boric acid, phosphoric acid, fluoroboric acid and/or a water-soluble or water-insoluble copper salt or zinc salt, or one or more of these compounds.

According to still another embodiment, the wood preservative further comprises at least one organic biocidal compound or a mixture of organic compounds that comprises an organic biocidal compound, the organic biocidal compound comprising at least one of a fungicide and an insecticide that is insoluble in water and soluble in an organic solvent or solvent mixture, and at least one of an emulsifier, a wetting agent, a dye and a pigment, an organic solvent or solvent mixture.

According to another preferred embodiment, the weight ratio of the mixture of (a) and/or (b) to the alkali metal fluorophosphate or ammonium fluorophosphate of the general formula $M_2PO_3F$ is about 20:1 to about 1:20, preferably about 10:1 to about 1:10.

According to another preferred embodiment, an aqueous and/or an organic solution of the wood preservative is used to treat wood or wood-based materials at a concentration of about 1.5% to about 7% strength by weight, preferably about 2% to about 5% strength by weight, under pressure and/or in a vacuum or double-vacuum process.

In another preferred embodiment of the present invention, an aqueous or organic solvent-containing solution of the wood preservative at a concentration of about 1% to about 35% strength by weight, preferably about 2% to about 25% strength by weight, is used for treating wood in a dipping, coating, rolling or spraying process.

In a further preferred embodiment of the present invention, the wood preservative is used as a coating agent which comprises about 1% to about 35% by weight, preferably about 2% to 25% by weight, of (a) at least one organic ammonium monofluorophosphate and/or one organic diammonium monofluorophosphate of the general formula $(R_1R_2R_3R_4N)R_5PO_3F$, and/or one of its mixtures of (b) and/or (c);

up to about 65% by weight, preferably up to about 40% by weight, relative to 100 parts by weight of (a), (b) and/or (c), may be replaced by another inorganic or organic biocide and/or wood preservative;

up to about 27% by weight, preferably about 0.5% to about 25% by weight, of at least one of a group consisting of a binder (calculated as a solid), a fixing agent and a plasticizer;

about 99% to about 32% by weight, preferably about 97.5% to about 50% by weight, of at least one diluent or diluent mixture that optionally contains at least one wetting agent and/or emulsifier and also, if appropriate, dyes and/or pigments and/or processing auxiliaries.

According to yet another preferred embodiment, a salt of monofluorophosphoric acid, preferably an alkali metal salt or an ammonium salt, is reacted with a benzyltrialkylammonium complex, preferably a benzyldimethylalkyl($C_8$-$C_{16}$, preferably $C_8$-$C_{12}$) ammonium complex, where the anion may be, inter alia, a halogen ion, sulfate ion, nitrate ion, hydroxyl ion and the like.

The present invention is further described below by reference to the following examples

EXAMPLES OF AGENTS FOR PRESERVING WOOD

EXAMPLE 1.

30 g of benzyldimethylalkyl($C_{12}$-$C_{14}$)ammonium chloride
6 g of $Na_2PO_3F$ are dissolved in
74 g of water at 19° C.
A clear solution was produced The resultant 36% strength solution of the wood preservative was employed in the dipping process for wood preservation.

EXAMPLE 2.

20 g of benzyldimethylalky($C_{12}$-$C_{14}$) ammonium chloride
10 g of $Na_2PO_3F$
2 g of $H_3BO_3$ and
58 g of water

EXAMPLE 3.

18 g of benzyldimethylalkyl($C_{12}$-$C_{14}$)ammonium chloride
10 g of $(NH_4)_2PO_3F$
1 g of $H_3BO_3$
1 g of wetting agent and
68 g of water

EXAMPLE 4.

25 g of an organic ammonium monfluorophosphate and/or an organic diammonium monofluorophosphate of the general formula $(R_1R_2R_3R_4N)R_5PO_3F$ in which $R_1$, $R_2$, $R_3$ and $R_4$ are identical or different and each denotes a straight-chain, branched or cyclic, saturated or unsaturated alkyl, aralkyl, alkyaryl or aryl radical, where these may optionally be substituted by alkyl, alkoxy or hydroxyl, and a maximum of three of the substituents may alternatively be hydrogen or together form an alkylene bridge,
3 g of $H_3BO_3$
0.5 g of dyes and
71 g of water

EXAMPLE 5.

20 g of an organic ammonium monofluorophosphate and/or an organic diammonium monofluorophosphate of the general formula $(R_1R_2R_3R_4N)R_5PO_3F$, in which $R_1$, $R_2$, $R_3$ and $R_4$ are identical or different and each denotes a straight-chain, branched or cyclic, saturated or unsaturated alkyl, aralkyl, alkylaryl or aryl radical, where these may optionally be substituted by alkyl, alkoxy or hydroxyl and a maximum of three of the substituents may alternatively by hydrogen or together form an alkylene bridge,
78 g of an isopropanol/water mixture and
2 g of dyes used in wood preservative paints.

What is claim is:

1. An agent for preserving wood or wood-based based materials comprising ammonium monofluorophosphate selected from the group consisting of
(1) at least one of components (a) and (b), and
(2) a mixture of components (a), (b) or mixtures thereof and component (c), wherein component
(a) comprises an organic ammonium monofluorophosphate an organic diammonium monofluorophosphate or mixtures thereof of the formula $(R_1R_2R_3R_4N)R_5PO_3F$     (Formula I)

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstituted or substituted by an alkyl, alkoxy or a hydroxyl group, and up to three of the four $R_1$-$R_4$ can be hydrogen or can together form an alkylene bridge;

$R_5$ is a hydrogen atom or a $R_6R_7R_8R_9N$ group in which R6, R7, R8 and R9, respectively, have the same meanings as $R_1$, $R_2$, $R_3$ and $R_4$, respectively;

(b) comprises a mixture of a salt of monofluorophosphoric acid in a solvent with at least one ammonium salt of the formula $R_1R_2R_3R_4NX$     (Formula II)

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $M_2PO_3F$, $MHPO_3F$ or mixtures thereof wherein M is at least one of sodium, potassium and ammonium.

2. An agent as claimed in claim 1, wherein the agent further comprises a component (d), said component (d) comprising at least one compound selected from the group consisting of a biocidal compound and a fire-inhibiting compound.

3. An agent as claimed in claim 1, wherein said agent further comprises (e) at least one compound selected from the group consisting of a wetting agent, an emulsifier, a dye and a pigment.

4. An agent as claimed in claim 2, wherein said agent further comprises (e) at least one compound selected from the group consisting of a wetting agent, an emulsifier, a dye and a pigment.

5. An agent as claimed in claim 3, wherein said ammonium monofluorophosphate is present in an amount of about 94% to about 99.95% by weight and component (e) is present in an total amount of about 0.05% to about 6% by weight.

6. An agent as claimed in claim 3, wherein said ammonium monofluorophosphate is present in an amount of about 96% to about 99.8% by weight and component (e) is present in an total amount of about 0.2% to about 4% by weight.

7. An agent as claimed in claim 4, wherein said ammonium monofluorophosphate is present in an amount of about 0.1% to about 80% by weight, component (d) is present in an amount of about 99.85% to about 15% by weight, and component (e) is present in an amount of about 0.05% to about 5% by weight.

8. An agent as claimed in claim 4, wherein said ammonium monofluorophosphate is present in an amount of about 10% to about 75% by weight, component (d) is present in an amount of about 89.9% to about 22% by weight, and component (e) is present in an amount of about 0.2% to about 3% by weight.

9. An agent as claimed in claim 2, wherein said biocidal compound is an inorganic or organic compound and said fire-inhibiting compound is an inorganic compound.

10. An agent as claimed in claim 2, wherein at least one of said biocidal compound and fire-inhibiting compound is comprised of at least one salt selected from the group consisting of an alkali metal salt, an ammonium salt, a magnesium salt, a copper salt and a zinc salt.

11. An agent as claimed in claim 10, wherein said one salt can be water-soluble, sparingly water-soluble or water-insoluble.

12. An agent as claimed in claim 10, wherein said one salt is selected from the group consisting of (a) an alkali metal salt of phosphoric acid, polyphosphoric acid, hydrofluoric acid, boric acid and fluoroboric acid and (b) an ammonium salt of phosphoric acid, polyphosphoric acid, hydrofluoric acid, boric acid and fluoroboric acid.

13. An agent as claimed in claim 10, wherein said salt of ammonium, magnesium, copper and zinc is selected from the group consisting of a chloride, a sulfate, a fluoride, a silicofluoride, a salt of boric acid, a salt of phosphoric acid and a salt of fluoroboric acid.

14. An agent as claimed in claim 1, wherein the agent further comprises a component (d), said component (d) comprising an organic biocidal compound or a mixture of organic compounds comprising an organic biocidal compound 15. An agent as claimed in claim 14, wherein said biocidal compound is a fungicide or an insecticide.

16. An agent as claimed in claim 14, wherein said biocidal compound is insoluble in water and soluble in an organic solvent or an organic solvent mixture.

17. An agent as claimed in claim 14, wherein said mixture further comprises (i) at least one of a group consisting of an emulsifier, a wetting agent, a dye and a pigment and (ii) an organic solvent or solvent mixture.

18. An agent as claimed in claim 1, wherein said agent comprises the monofluorophosphate represented by the formula $M_2PO_3F$ of component (c) and at least one of components (a) and (b), said ratio of (a), (b) or mixtures thereof to (c) is in the range of about 20:1 to 1:20.

19. An agent as claimed in claim 1, wherein said agent comprises the monofluorophosphate represented by the formula M2PO3F of component (c) and at least one of components (a) and (b), said ratio of (a), (b) or mixtures thereof to (c) is in the range of about 10:1 to 1:10.

20. An agent as claimed in claim 1, wherein said agent is an aqueous solution of about 1.5% to 7% strength by weight.

21. A method of preserving wood or wood-based materials comprising the step of treating said materials with an agent as defined by claim 1.

22. A method as claimed in claim 21, wherein said treatment is performed under pressure, vacuum or a combination thereof or double-vacuum process. a vacuum or double-vacuum process.

23. A method as claimed in claim 21, wherein said agent is in an aqueous solution of about 1.5% to about 7% strength by weight.

24. A method as claimed in claim 21, wherein said agent is in an aqueous or an organic solvent-containing solution of about 1% to about 38% strength by weight.

25. A coating agent for wood or wood-based materials comprising
ammonium monofluorophosphate selected from the group consisting of (1) at least one of components (a) and (b), and (2) a mixture of components (a), (b) or mixtures thereof and component (c),
component (d), and
component (e),
wherein component
(a) comprises an organic ammonium monofluorophosphate an organic diammonium monofluorophosphate or mixtures thereof of the formula $(R_1R_2R_3R_4N)R_5PO_3F$ (Formula I)

wherein $R_1$, $R_2$, $R_3$ and $R_4$ are identical or different and each denotes a straight-chain, branched or cyclic, saturated or unsaturated alkyl, aralkyl, alkylaryl or aryl radical, either unsubstitueed or substituted by an alkyl, alkoxy or a hydroxyl group, and up to three of the four $R_1$–$R_4$ can be hydrogen or can together form an alkylene bridge;

$R_5$ is a hydrogen atom or a $R_6R_7R_8R_9N$ group in which $R_6$, $R_7$, $R_8$ and $R_9$, respectively, have the same meanings as $R_1$, $R_2$, $R_3$ and $R_4$, respectively;

(b) comprises a mixture of a salt of monofluorophosphoric acid in a solvent with at least one ammonium salt of the formula $R_1R_2R_3R_4NX$ (Formula II)

wherein $R_1$, $R_2$, $R_3$ and $R_4$, respectively, have the same meanings as in Formula I, and X denotes an acid radical; and (c) comprises an alkali metal monofluorophosphate or ammonium monofluorophosphate of the formula $M_2PO_3F$, $MHPO_3F$ or mixtures thereof wherein M is at least one of sodium, potassium and ammonium;

(d) is optional and comprises at least one of a binder, a fixing agent and a plasticizer; and (e) comprises a diluent.

26. A coating agent as claimed in claim 25, wherein said ammonium monofluorophosphate is about 1% to 35% by weight, said component (d) is about 0% to about 27% by weight, and said component (e) is about 32% to about 99% by weight.

27. A coating agent as claimed in claim 26, wherein said ammonium monofluorophosphate is about 2% to 25% by weight, said component (d) is about 0.5% to 25% by weight, and said component (e) is about 50% to about 97.5% by weight.

28. A coating agent as claim in claim 26, further comprising at least one of an inorganic or organic biocide and another different wood preservative.

29. A method of using a coating agent comprising the step of applying said coating agent to the surface of a wood or wood-based material, wherein said coating agent is as defined by claim 25.

* * * * *